United States Patent
Park et al.

(10) Patent No.: US 12,023,408 B2
(45) Date of Patent: Jul. 2, 2024

(54) AMORPHOUS EFINACONAZOLE SOLID DISPERSION

(71) Applicant: DAEBONG LS CO., LTD., Incheon (KR)

(72) Inventors: Eun Ju Park, Hwaseong-si (KR); Hyun Ji, Siheung-si (KR); Ji Eun Lee, Busan (KR); Jin Oh Park, Seoul (KR)

(73) Assignee: DAEBONG LS CO., LTD., Incheon (KR)

( * ) Notice: Subject to any disclaimer, the term of this patent is extended or adjusted under 35 U.S.C. 154(b) by 0 days.

(21) Appl. No.: 17/762,272

(22) PCT Filed: Sep. 25, 2020

(86) PCT No.: PCT/KR2020/013164
§ 371 (c)(1),
(2) Date: Mar. 21, 2022

(87) PCT Pub. No.: WO2021/060950
PCT Pub. Date: Apr. 1, 2021

(65) Prior Publication Data
US 2022/0387323 A1    Dec. 8, 2022

(30) Foreign Application Priority Data
Sep. 26, 2019    (KR) .................. 10-2019-0118647

(51) Int. Cl.
*A61K 31/454* (2006.01)
*A61K 9/16* (2006.01)
*C07D 401/06* (2006.01)

(52) U.S. Cl.
CPC .......... *A61K 9/1652* (2013.01); *A61K 9/1635* (2013.01); *C07D 401/06* (2013.01); *C07B 2200/13* (2013.01)

(58) Field of Classification Search
None
See application file for complete search history.

(56) References Cited

U.S. PATENT DOCUMENTS

| 8,486,978 B2 | 7/2013 | Winckle et al. |
| 2016/0175335 A1* | 6/2016 | Nayar .................. A61K 31/69 |
| | | 514/64 |

FOREIGN PATENT DOCUMENTS

| KR | 10-1999-0044257 A | 6/1999 |
| KR | 10-2001-0098419 A | 11/2001 |

(Continued)

OTHER PUBLICATIONS

Hypromellose, Wikipedia. https://en.wikipedia.org/wiki/Hypromellose. pp. 1-5 (Year: 2023).*

(Continued)

*Primary Examiner* — Lakshmi S Channavajjala
(74) *Attorney, Agent, or Firm* — NKL LAW; Jae Youn Kim (57) ABSTRACT

A solid dispersion of amorphous efinaconazole and a method for preparing the same are proposed. The solid dispersion includes an amorphous form of efinaconazole and at least one stabilization carrier selected from hydroxypropyl methylcellulose (HPMC), hydroxypropyl cellulose (HPC), ethyl cellulose (EC), hydroxypropyl methylcellulose acetate succinate (HPMC-AS), polyvinylpyrrolidone (PVP), polyacrylic acid (PAA), saccharin, and malonic acid. The solid dispersion undergoes minimal thermodynamic deformation when exposed to ambient temperature and humidity, achieving improved stability, while maintaining the inherent improved stability and bioavailability of amorphous efinaconazole.

8 Claims, 13 Drawing Sheets

(56) References Cited

FOREIGN PATENT DOCUMENTS

| KR | 2016-0068812 A | 6/2016 | | |
|---|---|---|---|---|
| WO | WO-9744014 A1 | * | 11/1997 | ........... A61K 31/495 |
| WO | 2008081940 A1 | 7/2008 | | |

OTHER PUBLICATIONS

Vasconcelos et al., Solid dispersions as strategy to improve oral bioavailability of poor water soluble drugs. Drug Discovery Today, vol. 12(23/24), Dec. 2007, pp. 1068-1075 (Year: 2007).*

Jain et al. Solubility and dissolution enhancement strategies: current understanding and recent trends. Drug Development and Industrial Pharmacy. published online Oct. 24, 2014. Drug Dev Ind Pharm, 2015; 41(6): 875-887 (Year: 2015).*

Chowdary et al., "Dissolution Rate and Formulation Studies on Solid Dispersions of Itraconazole", Indian Journal of Pharmaceutical Sciences, Nov.-Dec. 2000, No. 62, vol. 6, pp. 471-474.

Mistry, P. et al., "Role of the strength of chug-polymer interactions on the molecular mobility and crystallization inhibition in ketoconazole solid dispersions", Molecular pharmaceutics, 2015, vol. 12, pp. 3339-3350.

Chen, Y. et al., "Initial drug dissolution from amorphous solid dispersions controlled by polymer dissolution and drug-polymer interaction", Pharmaceutical research, 2016, vol. 33, pp. 2445-2458.

Chowdary, K. P. R. et al., Dissolution rate and formulation studies on solid dispersions of itraconazole, Indian journal of pharmaceutical sciences, Nov.-Dec. 2000, vol. 62, No. 6, pp. 471-474.

* cited by examiner

AMORPHOUS EFINACONAZOLE SOLID DISPERSION

TECHNICAL FIELD

The present invention relates to a solid dispersion of amorphous efinaconazole and a method for preparing the same.

BACKGROUND ART

Efinaconazole is a triazole antifungal agent with proven therapeutic activity for onychomycosis.

Formulations useful for topical delivery of efinaconazole and other triazole antifungal drugs for the treatment of onychomycosis are described, for example, in U.S. Pat. No. 8,486,978 ("Patent Document 1").

However, some formulations containing triazole active ingredients exhibit varying degrees of instability during storage. Particularly, certain formulations were reported to discolor within storage periods as short as one or two days, resulting in composition colors ranging from yellow to deep red or brown (Korean Patent Publication No. 2016-0068812; "Patent Document 2"). Such discoloration can discourage the prescribed use of the compositions by patients who are reluctant to self-administer the discolored compositions.

Therefore, stabilization of efinaconazole formulations is a very important issue in this field.

(Patent Document 1) U.S. Pat. No. 8,486,978 B2 (Jul. 16, 2013)

(Patent Document 2) KR2016-0068812 A (Jun. 15, 2016)

DETAILED DESCRIPTION OF THE INVENTION

Problems to be Solved by the Invention

As is generally known, amorphous forms of drugs have greatly improved bioavailability and are suitable for short-acting drugs due to their high solubility. Despite these great advantages, amorphous forms have poor stability, are stored for a short period of time, and make control over the release and the blood concentration of drugs difficult due to their thermodynamical instability compared to crystalline forms.

Thus, the present invention intends to provide a stabilized formulation of amorphous efinaconazole.

Means for Solving the Problems

The present invention has been made in an effort to solve the problems of the prior art and provides a solid dispersion including an amorphous form of efinaconazole and at least one stabilization carrier selected from hydroxypropyl methylcellulose (HPMC), hydroxypropyl cellulose (HPC), ethyl cellulose (EC), hydroxypropyl methylcellulose acetate succinate (HPMC-AS), polyvinylpyrrolidone (PVP), polyacrylic acid (PAA), saccharin, and malonic acid.

The weight ratio of the efinaconazole to the stabilization carrier is 1:0.1 to 1:5.

Figure 1:
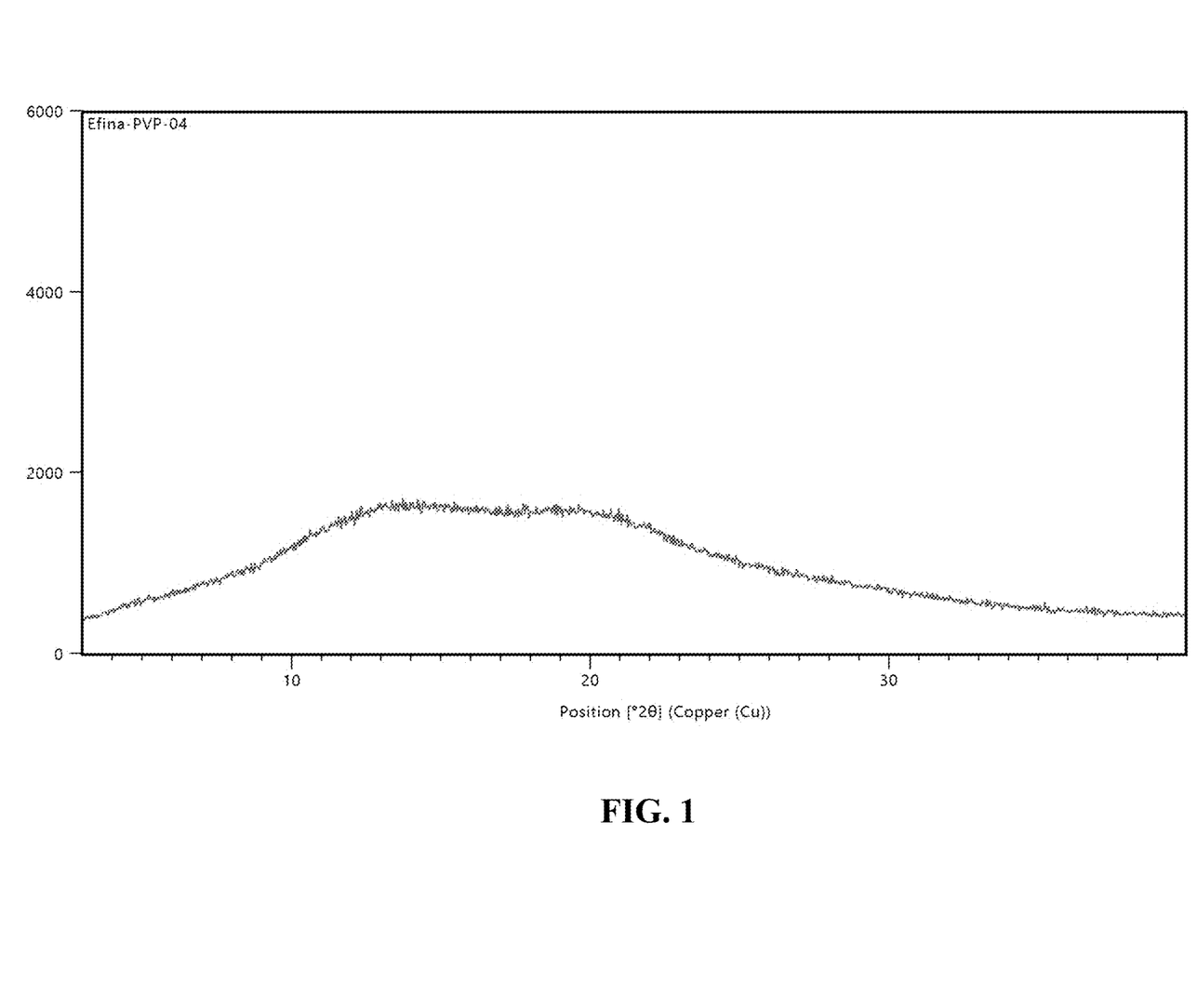
FIG. 1 is an XRPD pattern of a solid dispersion including an amorphous form of efinaconazole and polyvinylpyrrolidone (PVP) as its stabilization carrier.

The solid dispersion includes polyvinylpyrrolidone as the stabilization carrier and its crystal form has the XRPD pattern shown in FIG. 1.

Figure 3:
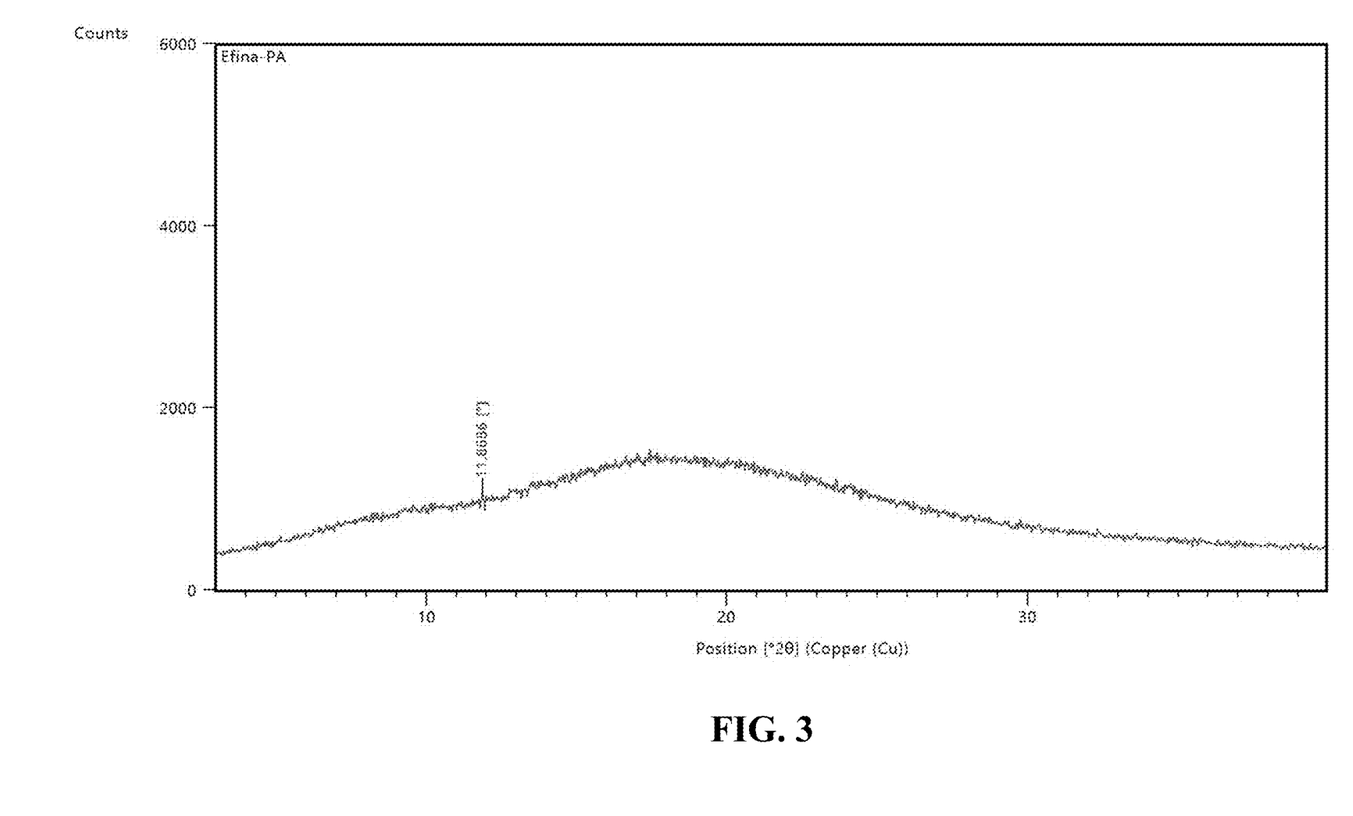
FIG. 3 is an XRPD pattern of a solid dispersion including an amorphous form of efinaconazole and polyacrylic acid (PAA) as its stabilization carrier.

The solid dispersion includes polyacrylic acid as the stabilization carrier and its crystal form has the XRPD pattern shown in FIG. 3.

Figure 5:
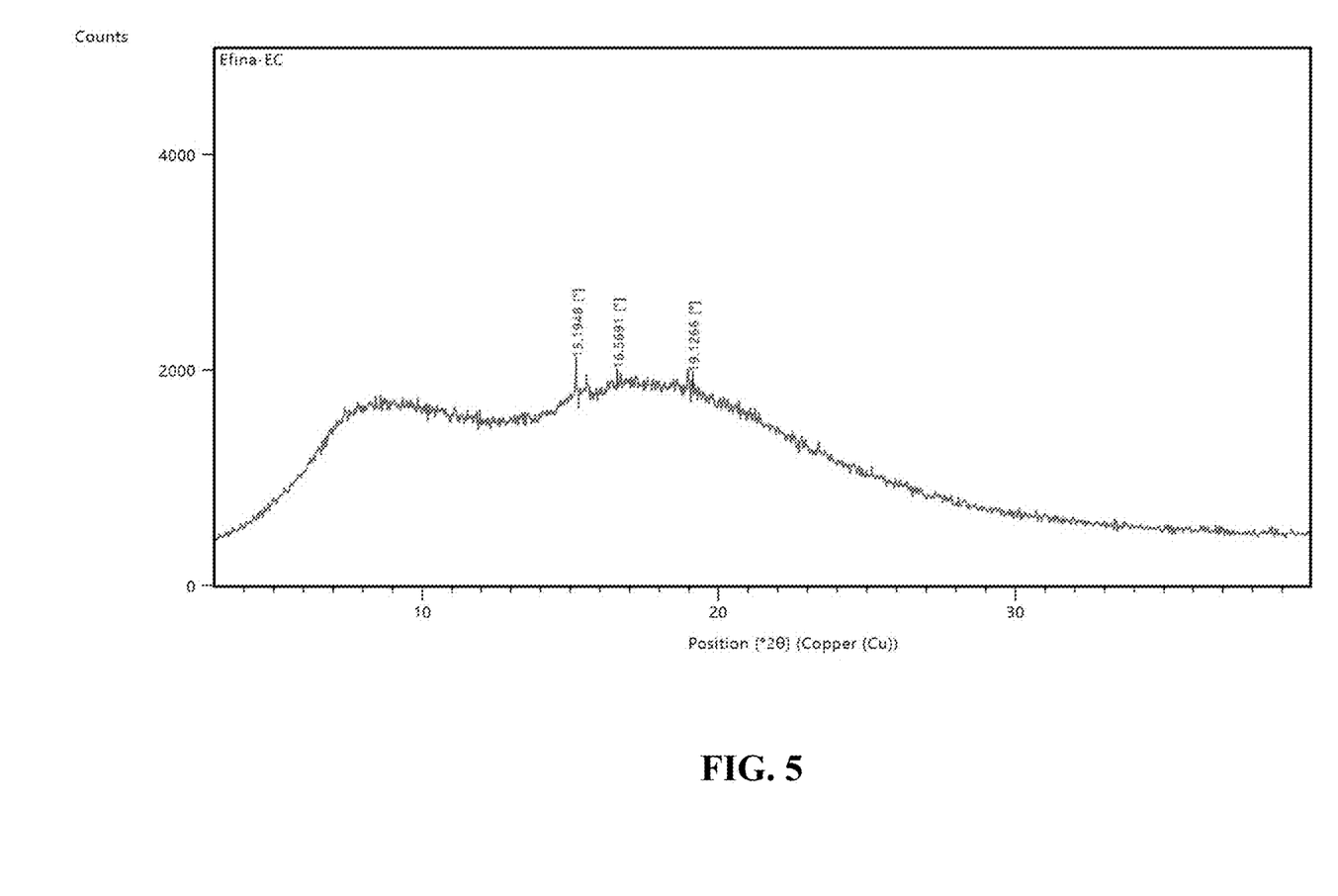
FIG. 5 is an XRPD pattern of a solid dispersion including an amorphous form of efinaconazole and ethyl cellulose as its stabilization carrier.

The solid dispersion includes ethyl cellulose as the stabilization carrier and its crystal form has the XRPD pattern shown in FIG. 5.

Figure 7:
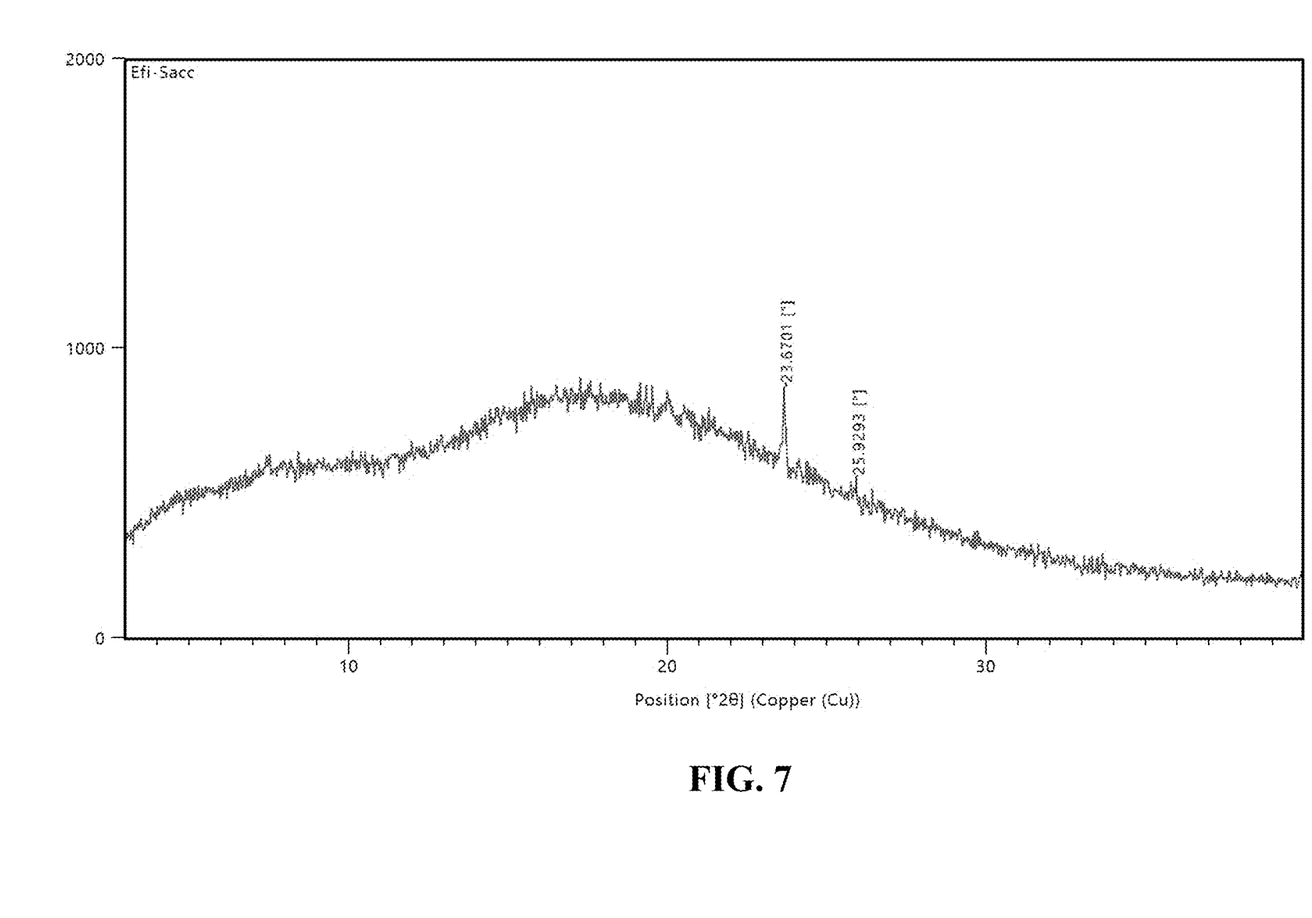
FIG. 7 is an XRPD pattern of a solid dispersion including an amorphous form of efinaconazole and saccharin as its stabilization carrier.

The solid dispersion includes saccharin as the stabilization carrier and its crystal form has the XRPD pattern shown in FIG. 7.

Figure 9:
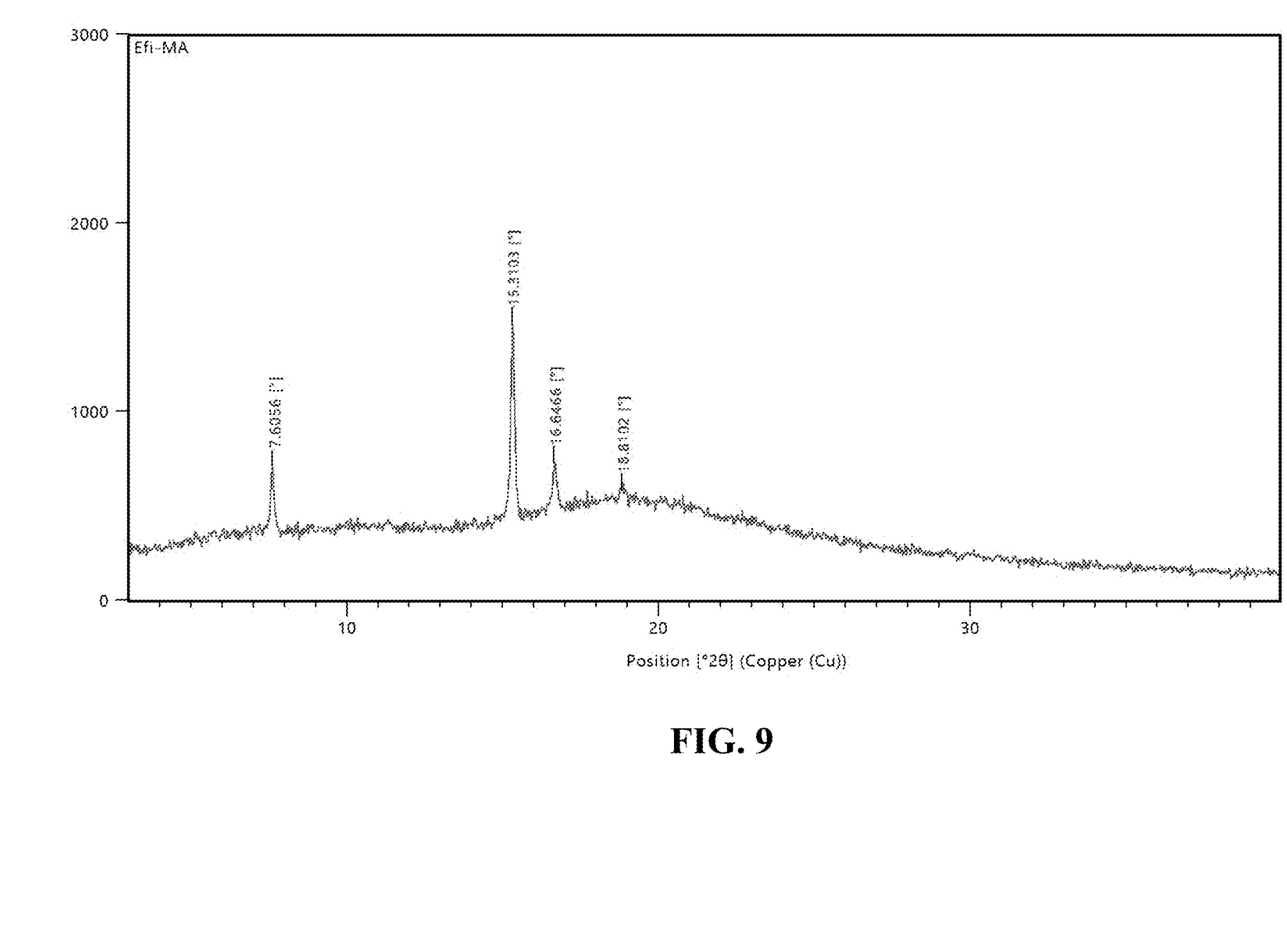
FIG. 9 is an XRPD pattern of a solid dispersion including an amorphous form of efinaconazole and malonic acid as its stabilization carrier.

The solid dispersion includes malonic acid as the stabilization carrier and its crystal form has the XRPD pattern shown in FIG. 9.

Figure 11:
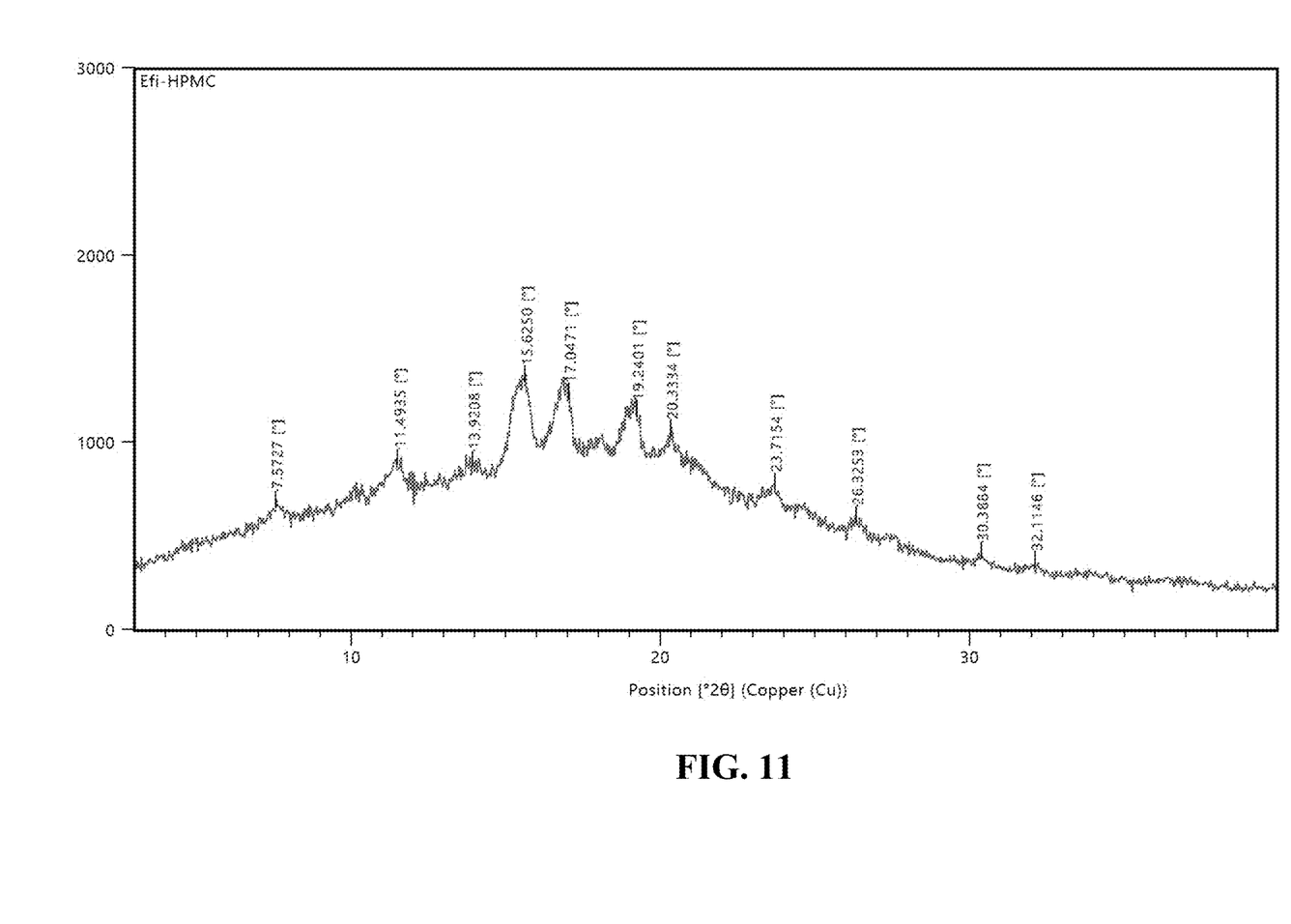
FIG. 11 is an XRPD pattern of a solid dispersion including an amorphous form of efinaconazole and hypromellose as its stabilization carrier.

The solid dispersion includes hypromellose as the stabilization carrier and its crystal form has the XRPD pattern shown in FIG. 11.

The present invention also provides a method for preparing a solid dispersion, including: dissolving efinaconazole and at least one stabilization carrier selected from hydroxypropyl methylcellulose (HPMC), hydroxypropyl cellulose (HPC), ethyl cellulose (EC), hydroxypropyl methylcellulose acetate succinate (HPMC-AS), polyvinylpyrrolidone (PVP), polyacrylic acid (PAA), saccharin, and malonic acid in a solvent; and filtering and drying the solution.

The solvent is a single solvent or a solvent mixture that has solubilities of at least 1 mg/ml for both the efinaconazole and the stabilization carrier.

The solvent is methanol, ethanol, isopropyl alcohol, n-propanol, isoamyl alcohol, acetone, ethyl methyl ketone, methyl isobutyl ketone, ethyl acetate, n-propyl acetate, n-butyl acetate, t-butyl acetate, toluene, dichloromethane, acetonitrile or a mixture thereof.

Effects of the Invention

The solid dispersion of the present invention undergoes minimal thermodynamic deformation when exposed to ambient temperature and humidity, achieving improved stability, while maintaining the inherent improved stability and bioavailability of amorphous efinaconazole.

BEST MODE FOR CARRYING OUT THE INVENTION

The present invention will now be described in detail.

One aspect of the present invention is directed to a solid dispersion including:

an amorphous form of efinaconazole; and at least one stabilization carrier selected from hydroxypropyl methylcellulose (HPMC), hydroxypropyl cellulose (HPC), ethyl cellulose (EC), hydroxypropyl methylcellulose acetate succinate (HPMC-AS), polyvinylpyrrolidone (PVP), polyacrylic acid (PAA), saccharin, and malonic acid.

As used herein, the term "solid dispersion" refers to a solid product that includes two or more different components forming a single system. Generally, a solid dispersion refers to a homogenous dispersion of a small amount of a dispersed phase in a large amount of a solid dispersion medium (corresponding to the stabilization carrier).

However, the amount of the dispersion medium is not limited as long as it is sufficient to contribute to the stabilization of the dispersed phase and may be smaller than that of the dispersed phase. In the present invention, the weight ratio of the efinaconazole as a dispersed phase to the stabilization carrier as a dispersion medium may be 1:0.1 to 1:5, preferably 1:0.3 to 1:4.

As used herein, the term "amorphous form of efinaconazole" refers to efinaconazole in a substantially amorphous solid state form. The term "substantially amorphous" means that preferably at least 80%, more preferably at least 90%, most preferably at least 95% of the drug as a dispersed phase is in an amorphous form.

As used herein, the term "amorphous solid" generally refers to a solid that possesses a crystal-like short-range molecular arrangement but lacks long-range orders in molecular packing, which can be found in crystalline solids.

Whether the efinaconazole is in an amorphous solid form can be determined by polarized light microscopy, X-ray powder diffraction (XRPD) or differential scanning calorimetry (DSC).

The stabilization carrier is selected from the group consisting of hydroxypropyl methylcellulose (HPMC), hydroxypropyl cellulose (HPC), ethyl cellulose (EC), hydroxypropyl methylcellulose acetate succinate (HPMC-AS), polyvinylpyrrolidone (PVP), polyacrylic acid (PAA), saccharin, and malonic acid.

The stabilization carrier forming the solid dispersion with the amorphous form of efinaconazole shows no characteristic X-ray powder diffraction peaks, contributing to maintaining the amorphous form.

The stabilization carrier enhances the stability of the efinaconazole and suppresses the formation of related substances, which can be understood in more detail through the following Examples section.

The solid dispersion can be prepared by dissolving the efinaconazole and the stabilization carrier in a suitable solvent to form a feed solution and filtering and drying the feed solution. It should be understood that the dried product can be pulverized into a powder and this pulverization does not change the crystallinity of the solid dispersion.

As used herein, the term "suitable solvent" refers to a solvent or a mixture of solvents that has sufficient solubilities, for example, solubilities of at least about 1 mg/ml for both the drug and the polymer. Different solvents may be required to achieve the desired solubilities for the drug and the stabilization polymer. In this case, a mixture of the different solvents is preferably used.

For example, the suitable solvent may be dichloromethane, chloroform, ethanol, methanol, 2-propanol, ethyl acetate, acetone, acetonitrile or a mixture thereof. The solvent is preferably acetonitrile, dichloromethane or methanol.

The drying is preferably performed under reduced pressure or vacuum for 12 to 24 hours.

The solid dispersion of the present invention is preferably prepared into pharmaceutical formulations. Examples of such pharmaceutical formulations include tablets, powders, capsules, transdermal patches, and solid formulations for oral administration.

The efinaconazole and the stabilization carrier are uniformly distributed in the amorphous solid dispersion. This uniform distribution ensures improved solubility of the solid dispersion and minimizes thermodynamic deformation caused by ambient temperature and humidity, leading to improved bioavailability of the efinaconazole while maintaining the stability of the amorphous form.

Due to these advantages, the applicability of the stable solid dispersion including amorphous efinaconazole according to the present invention can be extended to oral formulations and injectable formulations as well as topically applied formulations and transdermal absorption formulations unless it causes clinical problems. For reference, efinaconazole is currently used only as a topically applied agent.

The present invention will be more specifically explained with reference to the following examples. However, it is to be noted that these examples are not intended to limit the scope of the invention.

EXAMPLES

Example 1—Preparation of Solid Dispersion of Amorphous Efinaconazole and Polyvinylpyrrolidone (1:1 Ratio)

Figure 2:
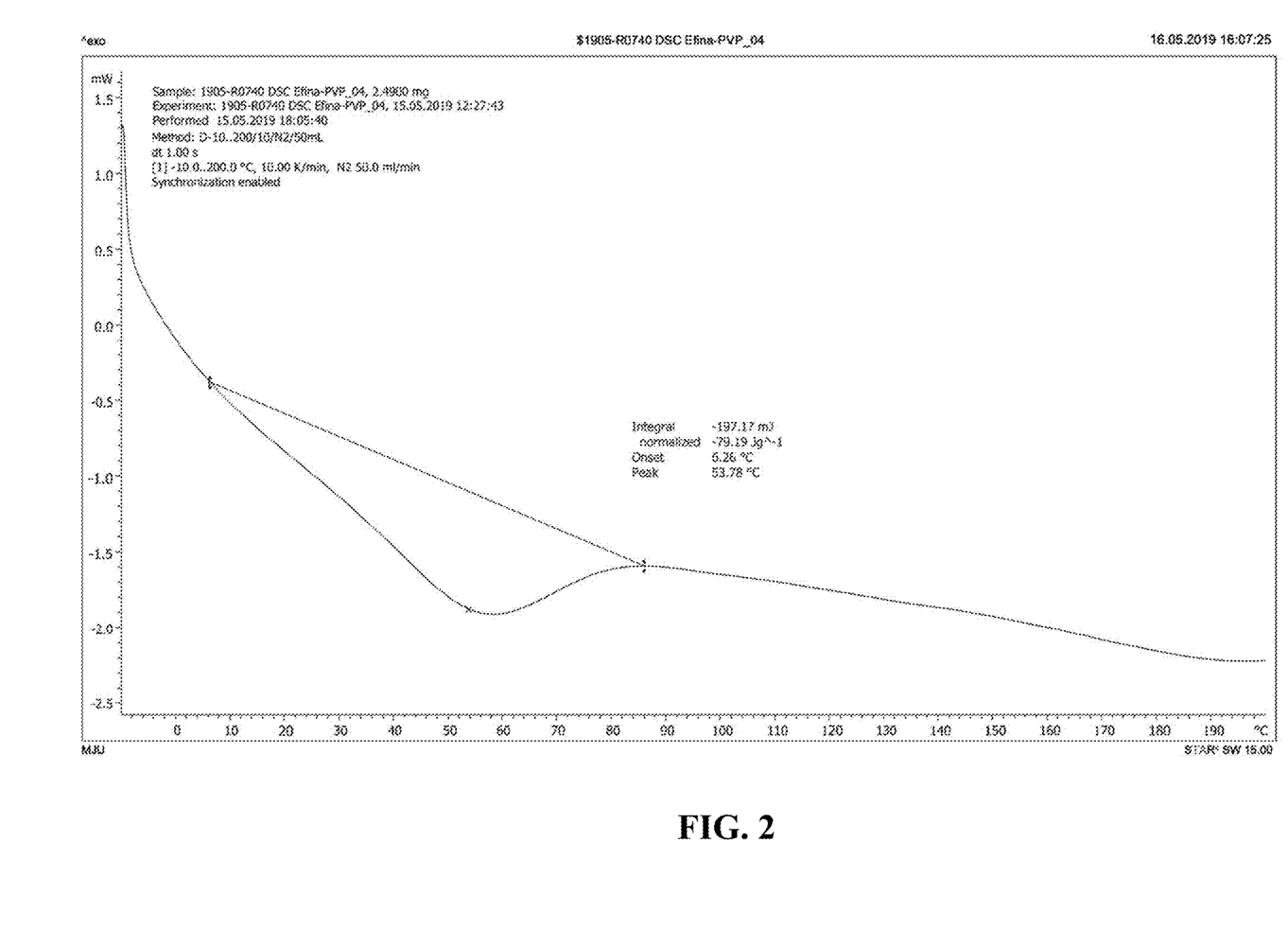
FIG. 2 is a DSC curve of a solid dispersion including an amorphous form of efinaconazole and polyvinylpyrrolidone (PVP) as its stabilization carrier.

0.1 g of (2R,3R)-2-(2,4-difluorophenyl)-3-(4-methylenepiperidin-1-yl)-1-(1H-1,2,4-triazol-1-yl)butan-2-ol, 0.1 g of polyvinylpyrrolidone, and 0.5 mL of dichloromethane were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 1 and 2.

Example 2—Preparation of Solid Dispersion of Amorphous Efinaconazole and Polyacrylic Acid (1:1 Ratio)

Figure 4:
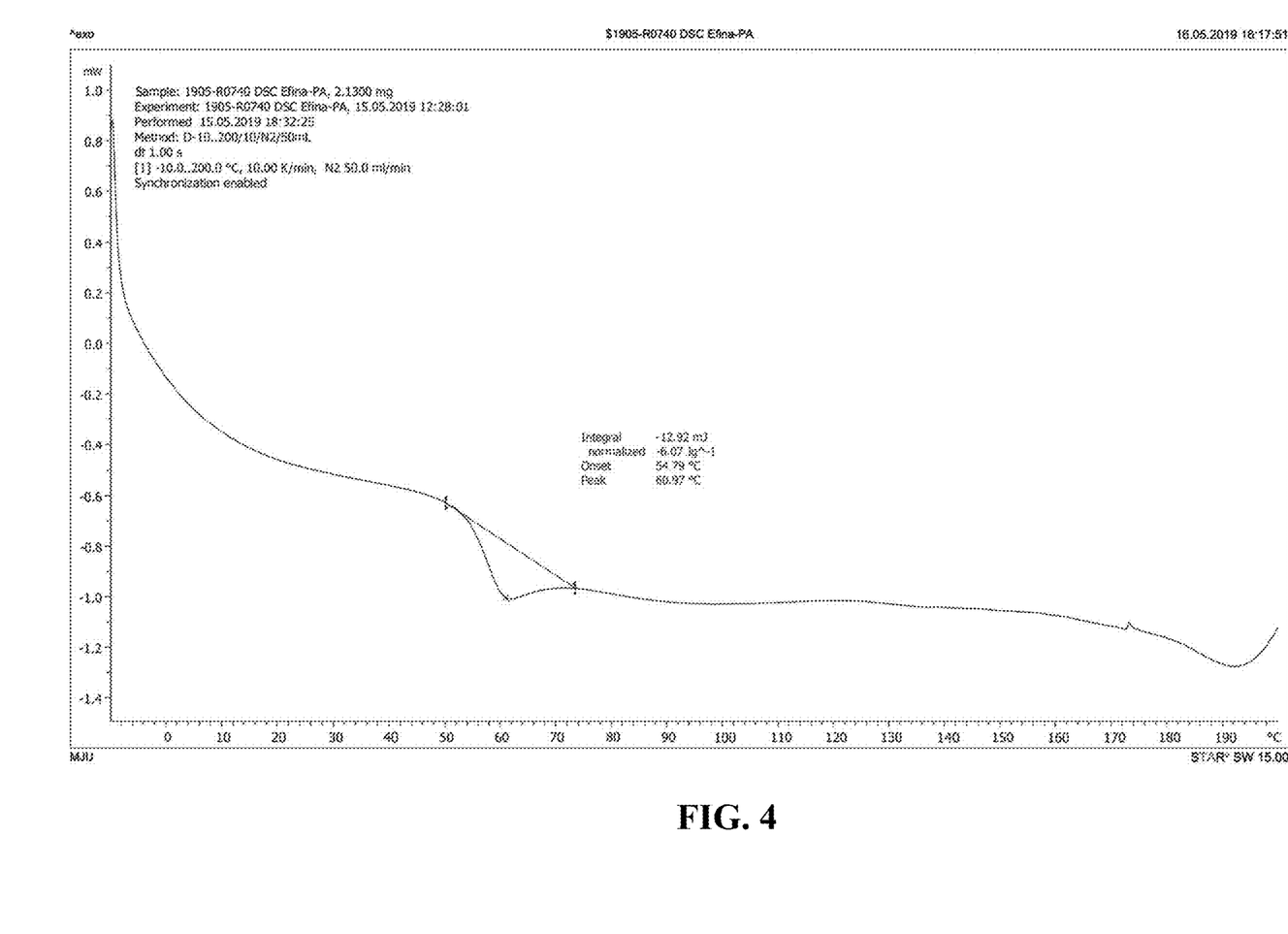
FIG. 4 is a DSC curve of a solid dispersion including an amorphous form of efinaconazole and polyacrylic acid (PAA) as its stabilization carrier.

0.1 g of (2R,3R)-2-(2,4-difluorophenyl)-3-(4-methylenepiperidin-1-yl)-1-(1H-1,2,4-triazol-1-yl)butan-2-ol, 0.1 g of polyacrylic acid, and 0.5 mL of methanol were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 3 and 4.

Example 3—Preparation of Solid Dispersion of Amorphous Efinaconazole and Ethyl Cellulose (1:1 Ratio)

Figure 6:
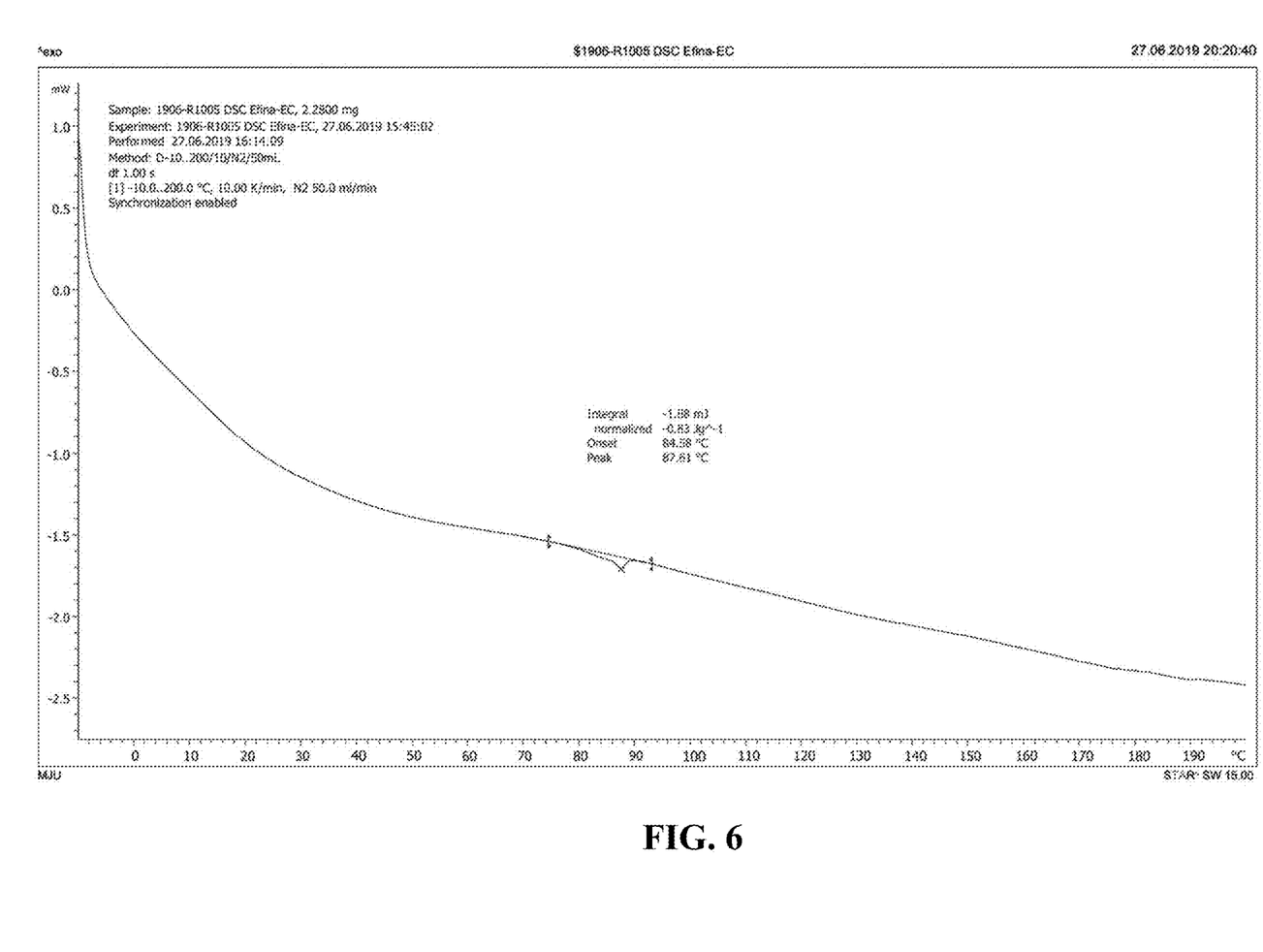
FIG. 6 is a DSC curve of a solid dispersion including an amorphous form of efinaconazole and ethyl cellulose as its stabilization carrier.

0.1 g of (2R,3R)-2-(2,4-difluorophenyl)-3-(4-methylenepiperidin-1-yl)-1-(1H-1,2,4-triazol-1-yl)butan-2-ol, 0.1 g of ethyl cellulose, and 0.5 mL of dichloromethane were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 5 and 6.

Example 4—Preparation of Solid Dispersion of Amorphous Efinaconazole and Saccharin (3:1 Ratio)

Figure 8:
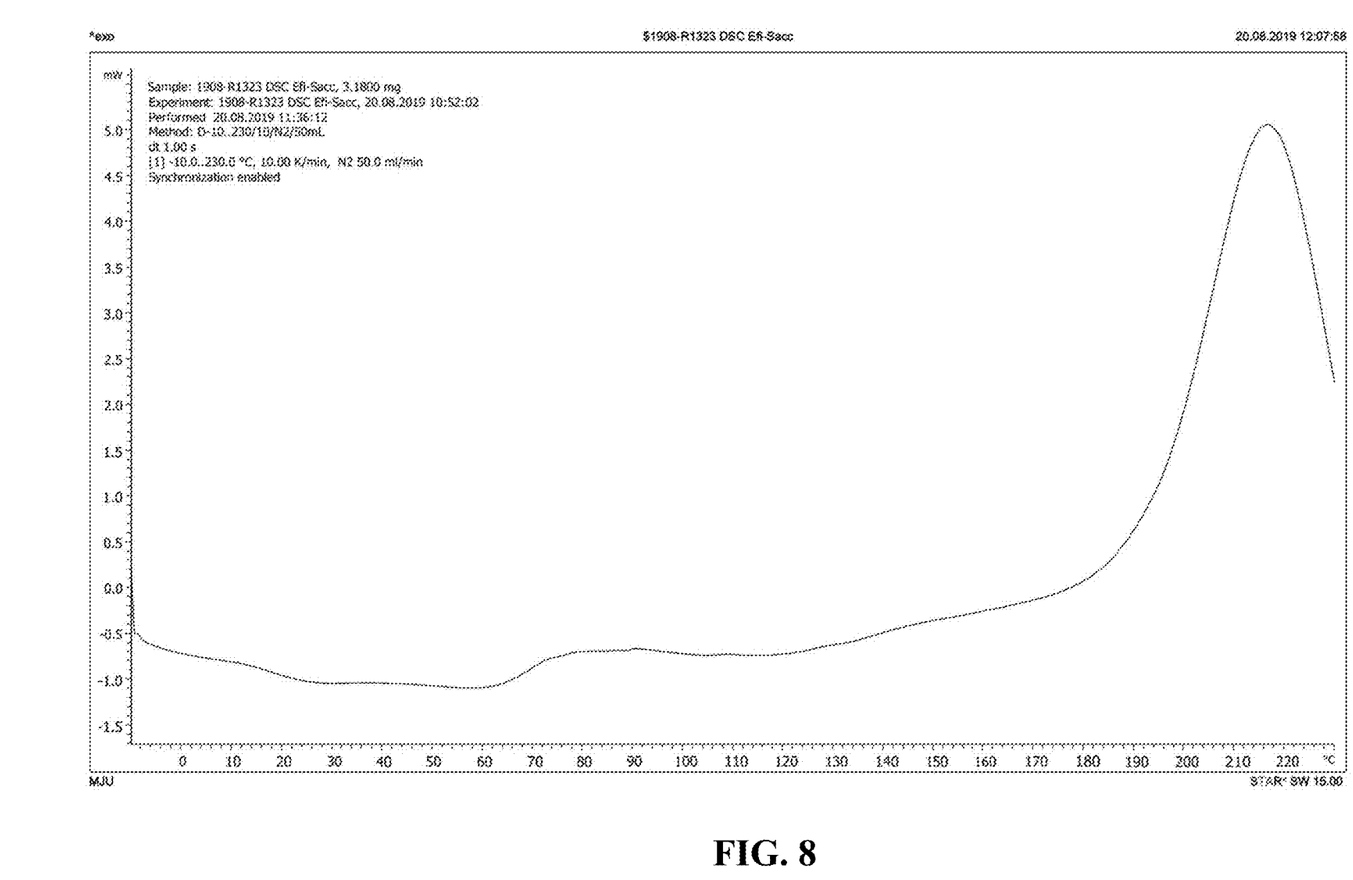
FIG. 8 is a DSC curve of a solid dispersion including an amorphous form of efinaconazole and saccharin as its stabilization carrier.

0.3 g of (2R,3R)-2-(2,4-difluorophenyl)-3-(4-methylenepiperidin-1-yl)-1-(1H-1,2,4-triazol-1-yl)butan-2-ol, 0.1 g of saccharin, and 0.9 mL of tetrahydrofuran were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 7 and 8.

Example 5—Preparation of Solid Dispersion of Amorphous Efinaconazole and Malonic Acid (3:1 Ratio)

Figure 10:
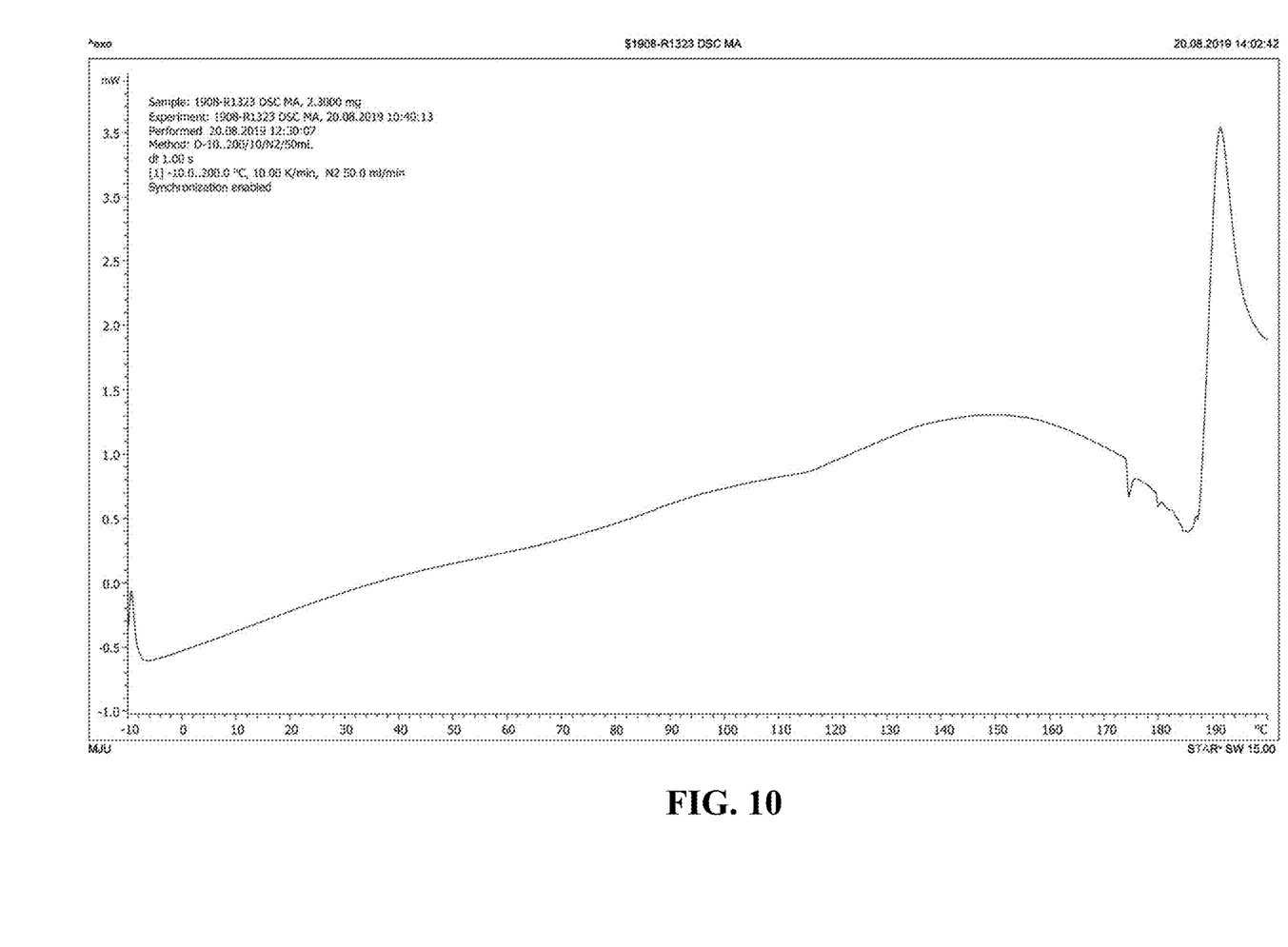
FIG. 10 is a DSC curve of a solid dispersion including an amorphous form of efinaconazole and malonic acid as its stabilization carrier.

0.3 g of (2R,3R)-2-(2,4-difluorophenyl)-3-(4-methylenepiperidin-1-yl)-1-(1H-1,2,4-triazol-1-yl)butan-2-ol, 0.1 g of malonic acid, and 0.9 mL of tetrahydrofuran were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 9 and 10.

Example 6—Preparation of Solid Dispersion of Amorphous Efinaconazole and Hypromellose (3:1 Ratio)

Figure 12:
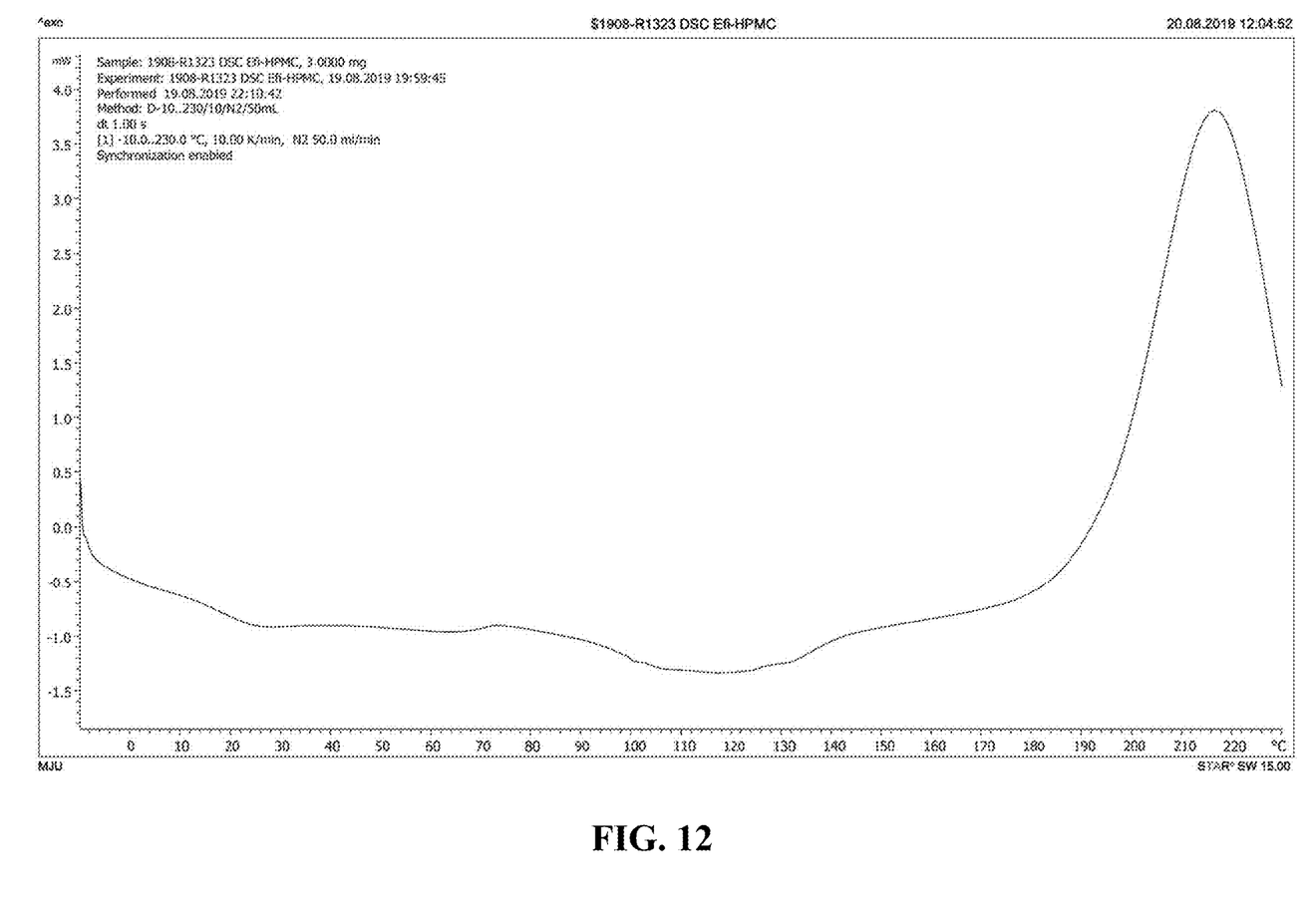
FIG. 12 is a DSC curve of a solid dispersion including an amorphous form of efinaconazole and hypromellose as its stabilization carrier.

0.3 g of (2R,3R)-2-(2,4-difluorophenyl)-3-(4-methylenepiperidin-1-yl)-1-(1H-1,2,4-triazol-1-yl)butan-2-ol, 0.1 g of hypromellose, and 0.9 mL of tetrahydrofuran were stirred in a flask at 23-28° C. for 1 h. The reaction solution was concentrated under reduced pressure to remove the solvent and dried under vacuum to obtain a solid dispersion in a crystalline form. The resulting crystal was analyzed by nuclear magnetic resonance spectroscopy, X-ray powder diffraction (XRPD), and differential scanning calorimetry (DSC). The results are shown in FIGS. 11 and 12.

Experimental Example 1—Test for the Content of Related Substances

The stabilities of the solid dispersions including amorphous efinaconazole (Examples 1-6) in solutions at different temperatures were investigated and compared with those of efinaconazole.

First, the solid dispersion prepared in Example 1 was dissolved in a solution and allowed to stand at different temperatures (at room temperature and in an oven at 65° C.) for different periods of time (1, 2, and 4 weeks). Thereafter, the contents of related substances were measured by high-performance liquid chromatography (HPLC). The same procedure was repeated except that crystalline efinaconazole was used instead of the solid dispersion.

Figure 13:
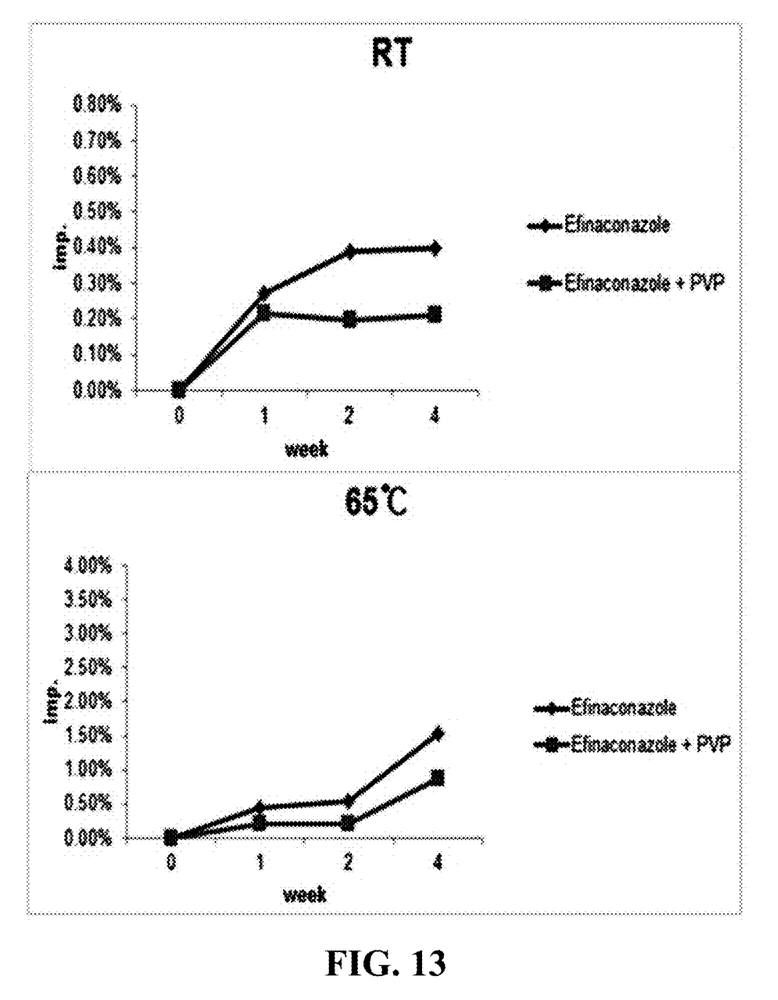
FIG. 13 shows changes in the content of related substances generated.

The results are shown in Table 1 and FIG. 13

TABLE 1

| | Room temperature | | | | 65° C. | | | |
|---|---|---|---|---|---|---|---|---|
| | 0 | 1 week | 2 weeks | 4 weeks | 0 | 1 week | 2 weeks | 4 weeks |
| Efinaconazole | 0 | 0.27% | 0.39% | 0.40% | 0 | 0.45% | 0.54% | 1.53% |
| Example 1 (Efinaconazole + PVP) | 0 | 0.21% | 0.20% | 0.21% | 0 | 0.20% | 0.20% | 0.86% |

As can be seen from the results in Table 1, the solid dispersion including amorphous efinaconazole (Example 1) was more stable than the crystalline efinaconazole. In addition, the solid dispersions were found to meet all standards and test specifications.

The invention claimed is:

1. An amorphous solid dispersion comprising an amorphous form of efinaconazole and at least one stabilization carrier selected from hydroxypropyl methylcellulose (HPMC), ethyl cellulose (EC), polyvinylpyrrolidone (PVP), polyacrylic acid (PAA), saccharin, and malonic acid.

2. The amorphous solid dispersion according to claim 1, wherein the weight ratio of the efinaconazole to the stabilization carrier is 1:0.1 to 1:5.

3. The amorphous solid dispersion according to claim 1, wherein the at least one stabilization carrier is the PVP and crystal form of the amorphous solid dispersion has an XRPD pattern as shown in FIG. 1.

4. The amorphous solid dispersion according to claim 1, wherein the at least one stabilization carrier is the PAA and crystal form of the amorphous solid dispersion has an XRPD pattern as shown in FIG. 3.

5. The amorphous solid dispersion according to claim 1, the at least one stabilization carrier is the EC and crystal form of the amorphous solid dispersion has an XRPD pattern as shown in FIG. 5.

6. The amorphous solid dispersion according to claim 1, the at least one stabilization carrier is the saccharin and crystal form of the amorphous solid dispersion has an XRPD pattern as shown in FIG. 7.

7. The amorphous solid dispersion according to claim 1, wherein the at least one stabilization carrier is the malonic acid and crystal form of the amorphous solid dispersion has an XRPD pattern as shown in FIG. 9.

8. The amorphous solid dispersion according to claim 1, wherein the at least one stabilization carrier is the HPMC and crystal form of the amorphous solid dispersion has an XRPD pattern as shown in FIG. 11.

* * * * *